US012564363B2

(12) United States Patent
Pulijala et al.

(10) Patent No.: US 12,564,363 B2
(45) Date of Patent: Mar. 3, 2026

(54) COUNTERBALANCING MECHANISM FOR A MOBILE RADIOGRAPHIC IMAGING APPARATUS

(71) Applicant: KONINKLIJKE PHILIPS N.V., Eindhoven (NL)

(72) Inventors: Sanjay Bharadwaj Pulijala, Pune (IN); K. N. Darshan, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 185 days.

(21) Appl. No.: 18/558,626

(22) PCT Filed: May 2, 2022

(86) PCT No.: PCT/EP2022/061704
§ 371 (c)(1),
(2) Date: Nov. 2, 2023

(87) PCT Pub. No.: WO2022/233781
PCT Pub. Date: Nov. 10, 2022

(65) Prior Publication Data
US 2024/0237957 A1 Jul. 18, 2024

(30) Foreign Application Priority Data

May 5, 2021 (IN) .............................. 202141020545
Jul. 27, 2021 (EP) .................................... 21187948

(51) Int. Cl.
*A61B 6/00* (2024.01)
(52) U.S. Cl.
CPC ............ *A61B 6/4405* (2013.01); *A61B 6/447* (2013.01); *A61B 6/4476* (2013.01)

(58) Field of Classification Search
CPC ...... A61B 6/4405; A61B 6/447; A61B 6/4476
See application file for complete search history.

(56) References Cited

U.S. PATENT DOCUMENTS 4,955,046 A * 9/1990 Siczek ................. A61B 6/4441
                                                                 378/197
2014/0098942 A1    4/2014 Omura
(Continued)

FOREIGN PATENT DOCUMENTS

EP         2859849 A1    4/2015
JP      2004033415 A    2/2004
(Continued)

OTHER PUBLICATIONS

PCT International Search Report, International application No. PCT/EP2022/061704, Jul. 29, 2022.

*Primary Examiner* — Kiho Kim
(74) *Attorney, Agent, or Firm* — Larry Liberchuk

(57) ABSTRACT

There is provided a positioning system for a mobile radiographic imaging apparatus. The positioning system comprises: a fixed column (31) mountable to a chassis of a transport cart, the fixed column supporting a collapsible column (24) that can be extended and retracted relative to the fixed column, the collapsible column supporting an arm assembly that can be translated relative to the collapsible column, the arm assembly being configured to support a radiographic head assembly; and a counterbalancing mechanism which is configured to counterbalance the collapsible column independently of the arm assembly and the radiographic head assembly.

14 Claims, 3 Drawing Sheets

(56)                    References Cited

U.S. PATENT DOCUMENTS

| | | | | |
|---|---|---|---|---|
| 2016/0015342 A1* | 1/2016 | Okuno | .................... | A61B 6/54 |
| | | | | 378/62 |
| 2016/0199013 A1 | 7/2016 | Moreno | | |
| 2019/0069860 A1 | 3/2019 | Takemoto | | |
| 2019/0069872 A1 | 3/2019 | Takemoto | | |
| 2019/0357863 A1 | 11/2019 | Dirisio | | |
| 2020/0148516 A1 | 5/2020 | Greilinger | | |

FOREIGN PATENT DOCUMENTS

| | | |
|---|---|---|
| WO | WO9014748 | 11/1990 |
| WO | WO2019069521 A1 | 11/2019 |

* cited by examiner

COUNTERBALANCING MECHANISM FOR A MOBILE RADIOGRAPHIC IMAGING APPARATUS

FIELD OF THE INVENTION

The invention relates to the field of radiography, more particularly to a mobile radiographic imaging apparatus, and more particularly to counterbalancing in a mobile radiographic imaging apparatus having a collapsible column supporting an arm assembly of adjustable height.

BACKGROUND OF THE INVENTION

Mobile radiographic imaging apparatuses typically comprise a transport cart supporting a collapsible column which holds a radiographic imaging device. The apparatus needs to be mechanically balanced in all possible configurations. Current counterbalancing mechanisms comprise different combinations of springs, counterweights, and feedback-controlled motors to counterbalance the radiographic imaging device over the required operating range. Such balancing mechanisms add weight and bulk to the mobile radiographic imaging apparatuses, making them difficult to operate on hospital premises.

SUMMARY OF THE INVENTION

There is therefore a need for improved counterbalancing mechanisms for mobile radiographic apparatuses, preferably those which are lighter and/or more compact. This need is met by the subject-matter of the independent claims. Optional features are set forth by the dependent claims.

According to a first aspect, there is provided a positioning system for a mobile radiographic imaging apparatus. The positioning system comprises: a fixed column mountable to a chassis of a transport cart, the fixed column supporting a collapsible column that can be extended and retracted relative to the fixed column, the collapsible column supporting an arm assembly that can be translated relative to the collapsible column, the arm assembly being configured to support a radiographic head assembly; and a counterbalancing mechanism which is configured to counterbalance the collapsible column independently of the arm assembly together with the head assembly.

Providing balancing to the collapsible column and to the arm assembly independently assists in reducing the complexity of the design and implementing the system by simpler means, thus allowing the system to be made more compact.

The counterbalancing mechanism may comprise a column balancer assembly configured to counterbalance the collapsible column and a separate arm balancer assembly configured to counterbalance the arm assembly together with the head assembly, wherein the column balancer assembly and the arm balancer assembly are independently operable. Providing two separate balancer assemblies rather than one single assembly may assist in reducing the weight and footprint of the counterbalancing mechanism.

The column balancer assembly may comprise a first tensioning element attached to a first cable, while the arm balancer assembly comprises a second tensioning element attached to a second cable, and wherein the first cable is able to move independently of the second cable. In this way, the column balancer assembly is readily able to operate independently of the arm balancer assembly. By "cable" is meant any appropriate means of transferring force including for example a wire rope. The tensioning elements as described herein include in particular spring balancers and more particularly those comprising spiral springs and variable radius pulleys, but it will be understood that the invention is not so limited and that any appropriate means of applying a constant force or tension may be used, including for example constant force springs (combined with fixed radius pulleys, for example). Equally, spring types other than spiral springs may be used such as tension springs. Any constant force mechanism configured to convert a force which varies with extension to a constant force may be used in place of the variable radius pulleys described herein, such as fusees, or dual-pulley arrangements, for example. Variable radius pulleys may be implemented using cam surfaces, conical and/or spiral sections, or expanding diameter mechanisms, for example.

The first tensioning element may comprise a first spring balancer configured to counter the weight of the collapsible column, and wherein the second tensioning element comprises a second spring balancer configured to counter the weight of the arm assembly together with the head assembly. The use of spring balancers provides for ready implementation of the positioning system using off-the-shelf components.

The first spring balancer may comprises a first spiral spring and a first variable radius pulley configured to convert the force exerted by the first spiral spring into a constant force, and wherein the second spring balancer comprises a second spiral spring and a second variable radius pulley configured to convert the force exerted by the second spiral spring into a constant force. Use of constant force in this way allows the collapsible column and/or arm assembly to remain in position once repositioned by the user.

The positioning system may feature an absence of tensioning elements in the collapsible column and in the arm assembly. In particular, the first and second tensioning elements may be mounted to, and/or at least partially housed within, the fixed column. Thus the collapsible column and the arm assembly are made lighter and the weight and footprint of the positioning system may be reduced by using smaller tensioning elements.

One of the first and second tensioning elements may be positioned substantially above the other of the first and second tensioning elements for reducing system footprint.

The column balancer assembly may comprise a first variable radius pulley, wherein the arm balancer assembly comprises a second variable radius pulley, and wherein the first and second variable radius pulleys are mounted to the fixed column, and only to the fixed column. The first and second variable radius pulleys may be at least partially housed within the fixed column. The positioning system may thereby feature an absence of variable radius pulleys that are mounted to the collapsible column and/or to the arm assembly. Mounting of further components of the balancer assemblies to the fixed column in this way allows for further reductions in the weight of the collapsible column and arm assembly.

The counterbalancing mechanism may be configured to underbalance one of the collapsible column and the arm assembly together with the head assembly and to overbalance the other of the collapsible column and the arm assembly together with the head assembly, to implement a desired sequence of motion when the positioning system is reconfigured by a user so as to reposition the head assembly. The sequencing is thus advantageously achieved by mechanical tuning rather than using motorized sequencing.

The underbalancing and overbalancing may be implemented in such a way that, in use, the mobile radiographic imaging apparatus remains statically balanced using the support of friction, although brakes may nonetheless be used to secure the positioning system in a particular configuration.

The positioning system may further comprise an assistive motor configured to assist a user in repositioning the head assembly. The motor may be arranged to drive the arm assembly via its coupling to the cable of the arm assembly, for example. The motor may be configured to receive feedback indicating the motion intended by the user from an appropriately-positioned force sensor, for example a force sensor positioned to sense a force imparted by a user for repositioning the radiographic head assembly using the positioning system. According to the present disclosure, less power is consumed by the assistive motor as the weight of the column is counterbalanced.

The positioning system may be configured to provide static balancing of the mobile radiographic imaging apparatus in all configurations of the positioning system.

The first aspect could also be described in terms of two stage independent balancing of a collapsible vertical column for mobile x-ray devices.

According to a second aspect, there is provided a mobile radiography system comprising the positioning system of any preceding claim and one or more of: a transport cart having a chassis to which the fixed column of the positioning system is mounted; and a radiographic head assembly supported by the arm assembly of the positioning system.

The invention may include one or more aspects, examples or features in isolation or combination whether or not specifically disclosed in that combination or in isolation. Any optional feature or sub-aspect of one of the above aspects applies as appropriate to any of the other aspects.

These and other aspects of the invention will be apparent from and elucidated with reference to the embodiments described hereinafter.

BRIEF DESCRIPTION OF THE DRAWINGS

A detailed description will now be given, by way of example only, with reference to the accompanying drawings, in which.

DETAILED DESCRIPTION OF EMBODIMENTS

Figure 1:
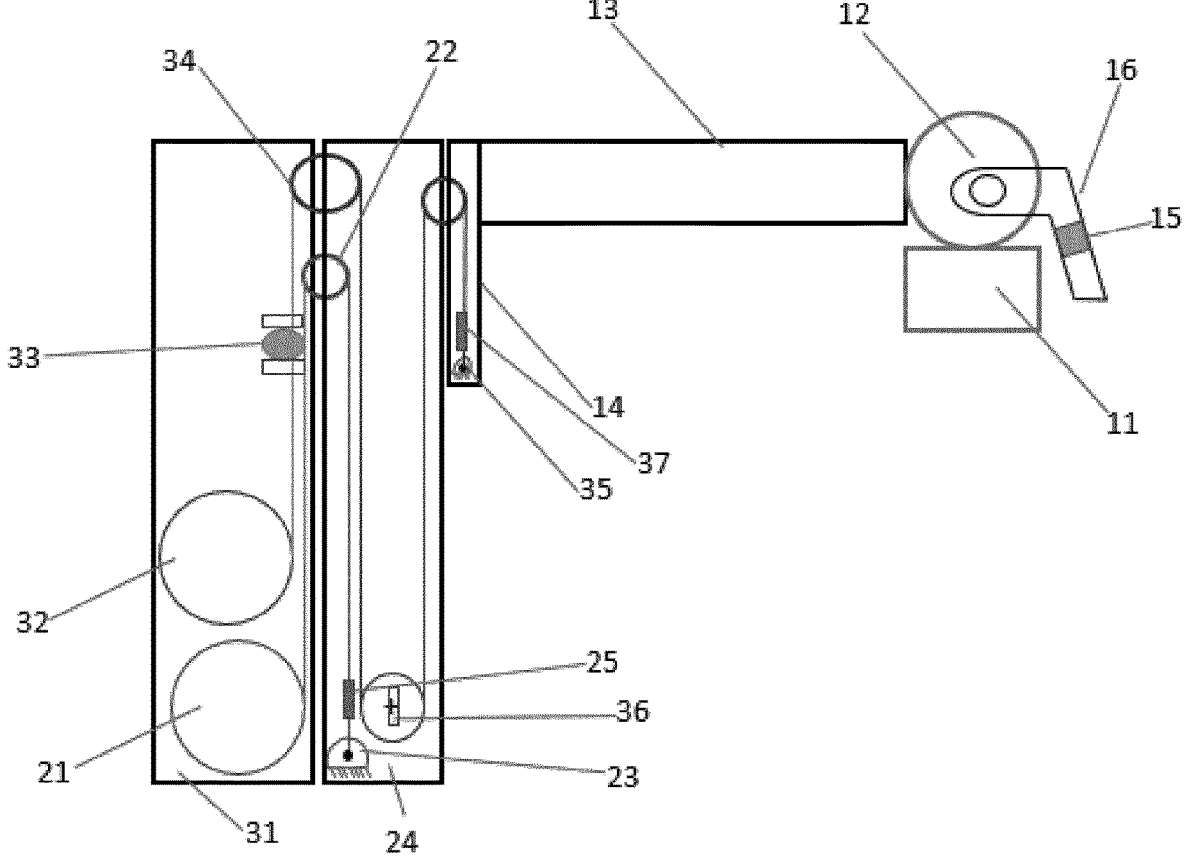
FIG. 1 illustrates a positioning assembly for a mobile radiographic apparatus according to the present disclosure.

FIG. 1 illustrates a positioning assembly for a mobile radiographic apparatus according to the present disclosure. The positioning assembly comprises a fixed column 31 which supports a collapsible column 24 that can be vertically extended and retracted relative to the fixed column 31. The collapsible column 24 in turn supports an arm assembly that can be vertically translated relative to the collapsible column 24. The arm assembly comprises a carriage 14 to which a telescopic arm 13 is mounted. The arm 13 is configured to support a head assembly. For the purposes of illustration, FIG. 1 illustrates a head assembly comprising an x-ray tube 12 and a collimator 11. The fixed column 31 is mountable to the chassis of a transport cart (not shown for convenience of illustration) for providing the mobile radiographic apparatus with its mobility.

Figure 2:
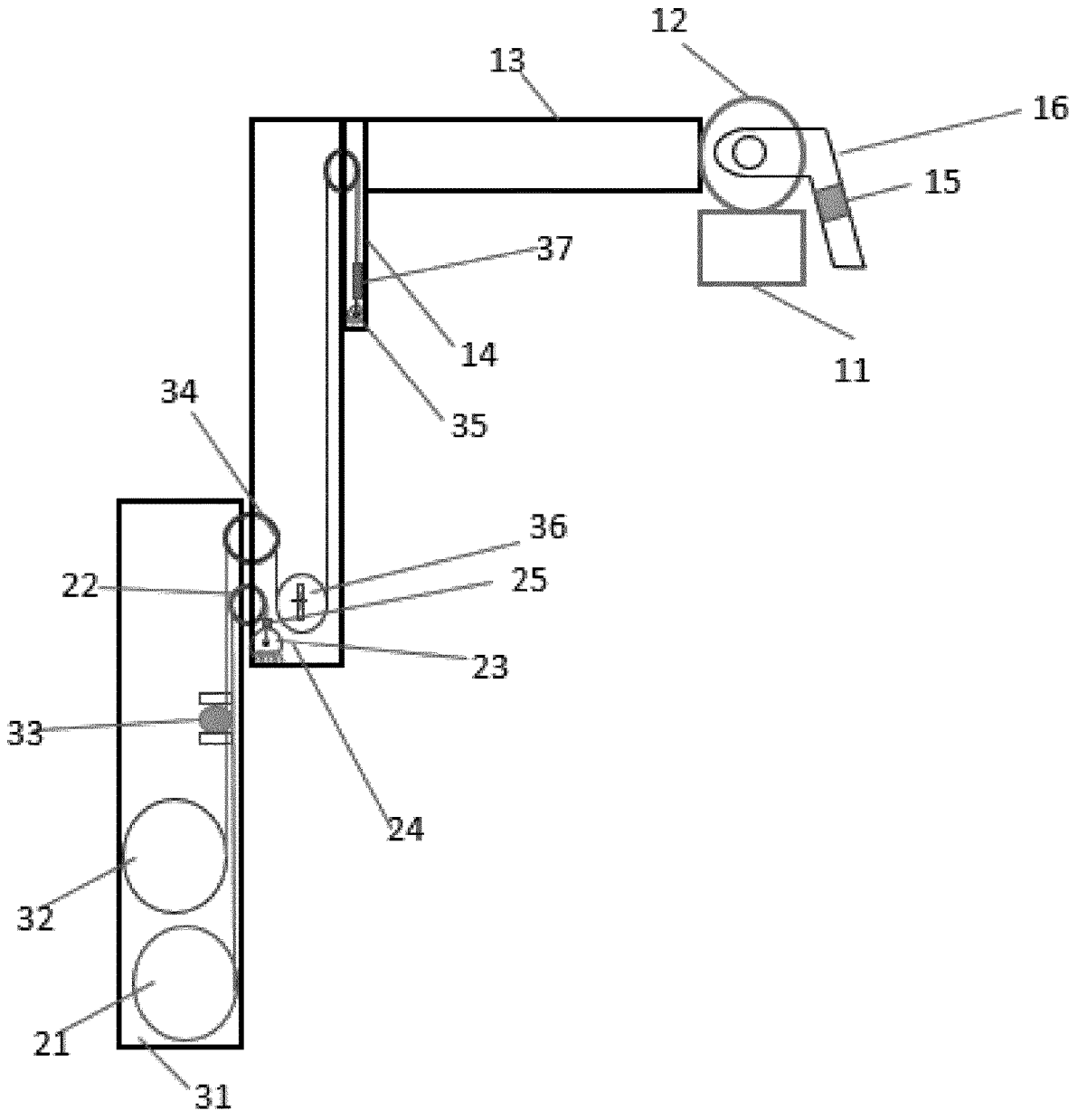
FIG. 2 illustrates the positioning assembly of FIG. 1 in its uppermost configuration.
Figure 3:
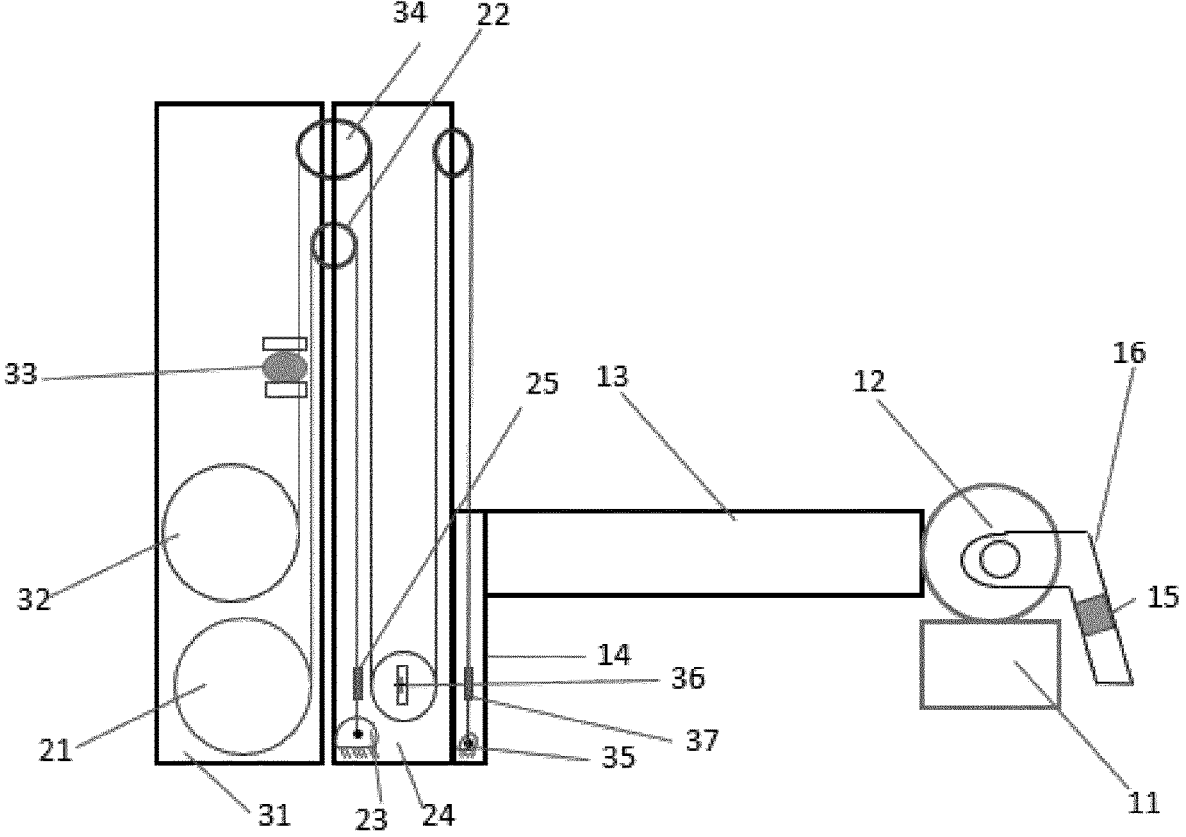
FIG. 3 illustrates the positioning assembly of FIG. 1 in its lowermost configuration.

The positioning assembly is shown in FIG. 1 in a parked configuration. In use, the positioning assembly is movable into further configurations for appropriate positioning of the head assembly relative to a patient. FIG. 2 illustrates the positioning assembly in its uppermost configuration, in which the carriage 14 is positioned at the uppermost end of its range of motion relative to the collapsible column 24, which is in turn positioned at the uppermost end of its range of motion with respect to the fixed column 31. FIG. 3 illustrates the positioning assembly in its lowermost configuration, in which both the carriage 14 and the collapsible column 24 are positioned at the lowermost ends of their respective ranges of motion.

The positioning system comprises a counterbalancing mechanism which is configured to balance the collapsible column 24 and the arm assembly separately. In particular, the counterbalancing mechanism comprises both a column balancer assembly and a carriage balancer assembly which are independently operable. In the illustrated embodiment, the column balancer assembly comprises a first spring balancer configured to counter the weight of the collapsible column 24 (and only the collapsible column 24) while the carriage balancer assembly comprises a second spring balancer configured to counter the weight of the arm assembly plus that of the head assembly (and only the weight of the arm assembly plus that of the head assembly). The counterbalancing mechanism is configured to provide static balancing of the apparatus in all of its possible configurations, thus assisting the user in reconfiguring the positioning system so as to reposition the head assembly for medical imaging.

The first spring balancer comprises a first spiral spring 21 together with a first variable radius pulley 22 configured to convert the force exerted by the first spiral spring 21 into a constant force. The first spiral spring 21 is affixed at its first end to an interior surface of the fixed column 31. The second end of the first spiral spring 21 is attached to a first cable which extends upwardly through the interior of the fixed column 31 and loops over the first variable radius pulley 22 before extending downwardly through the interior of the collapsible column 24 and attaching to a first anchor point or terminal 23 on an interior surface of the collapsible column 24 via a first safety latch 25 The first safety latch 25 actuates in response to cable breakage to prevent the collapsible column 24 from falling down.

The second spring balancer comprises a second spiral spring 32 together with a second variable radius pulley 34 configured to convert the force exerted by the second spiral spring 32 into a constant force. The second spiral spring 32 is affixed at its first end to an interior surface of the fixed column 31. The second end of the second spiral spring 32 is attached to a second cable which extends upwardly through the interior of the fixed column 31 and loops over the second variable radius pulley 34, before extending downwardly through the interior of the collapsible column 24 and looping under a first fixed radius pulley. From there the second cable extends upwardly again and loops over a second fixed radius pulley, before extending downwardly through the interior of the carriage 14 and attaching to a second anchor point 35 on an interior surface of the carriage 14 via a second safety latch 37. The first and second fixed radius pulleys are mounted to the collapsible column 24, the first by way of a safety latch 36.

It will be apparent that the first spring balancer functions independently of the second spring balancer. The two cables are separate and not interconnected in any way. In this way, the collapsible column and the arm assembly may be reconfigured independently of each other.

For ease of use, a desirable sequence of motion may be achieved by slightly underbalancing the collapsible column 24 and slightly overbalancing the arm assembly plus head assembly. This is implemented in such a way that the apparatus is still balanced statically using the support of friction. Nonetheless, the positioning system may comprise brakes configured to hold the positioning system in a specific configuration during imaging or transport, to ensure that the configuration does not shift due to external factors. For example, permanent magnet brakes may be used for this purpose. The magnitude of the underbalancing and overbalancing may amount to only a few Newtons of force (e.g., <3N). Alternatively, the counterbalancing mechanism may counterbalance the collapsible column 24 and arm assembly plus head assembly perfectly, with an imbalance being introduced by adding a small weight to achieve the desired sequence of movements. In typical existing positioning systems, 20-30N of force may be needed to initiate the movement, so a 3N imbalance should not affect the balancing.

The effort required to move the arm assembly downwardly is compensated by an assistive motor 33, which is coupled only to the first cable of the carriage balancer assembly. A force sensor 15 integrated into a handle 16 used to position the position system provides feedback to the motor 33. Motor assistance may be used when the arm assembly is moved from the parked position (FIG. 1) to the lowermost position (FIG. 2), to overcome the overbalancing applied to the arm assembly.

It will be noted that no tensioning element is located in either the collapsible column 24 or the arm assembly, according to the present disclosure. Thus, since neither of the first and second spring balancers is required to counter the weight of the other, the spring balancers may be smaller, reducing the overall weight and footprint of the positioning system. Additionally, both variable radius pulleys 22, 34 are mounted to the fixed column 31 and housed within the fixed column 31 to the largest possible extent, thereby further reducing the weight of the collapsible column 24 and arm assembly. Moreover, the second spiral spring 32 is positioned above the first 21 within the first column 31, allowing the footprint of the system to be reduced.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features.

It has to be noted that embodiments of the invention are described with reference to different categories. In particular, some examples are described with reference to methods whereas others are described with reference to apparatus. However, a person skilled in the art will gather from the description that, unless otherwise notified, in addition to any combination of features belonging to one category, also any combination between features relating to different category is considered to be disclosed by this application. However, all features can be combined to provide synergetic effects that are more than the simple summation of the features.

While the invention has been illustrated and described in detail in the drawings and foregoing description, such illustration and description are to be considered exemplary and not restrictive. The invention is not limited to the disclosed embodiments. Other variations to the disclosed embodiments can be understood and effected by those skilled in the art, from a study of the drawings, the disclosure, and the appended claims.

The word "comprising" does not exclude other elements or steps.

The indefinite article "a" or "an" does not exclude a plurality. In addition, the articles "a" and "an" as used herein should generally be construed to mean "one or more" unless specified otherwise or clear from the context to be directed to a singular form.

The mere fact that certain measures are recited in mutually different dependent claims does not indicate that a combination of these measures cannot be used advantageously.

Any reference signs in the claims should not be construed as limiting the scope.

Unless specified otherwise, or clear from the context, the phrase "A and/or B" as used herein is intended to mean all possible permutations of one or more of the listed items. That is, the phrase "X comprises A and/or B" is satisfied by any of the following instances: X comprises A; X comprises B; or X comprises both A and B.

The invention claimed is:

1. A positioning system for a mobile radiographic imaging apparatus, the positioning system comprising:
   a fixed column mountable to a chassis of a transport cart, the fixed column supporting a collapsible column that can be extended and retracted relative to the fixed column, the collapsible column supporting an arm assembly that can be translated relative to the collapsible column, the arm assembly being configured to support a radiographic head assembly; and
   a counterbalancing mechanism which is configured to counterbalance the collapsible column independently of the arm assembly together with the head assembly, wherein the counterbalancing mechanism is configured to underbalance the collapsible column and the arm assembly together with the radiographic head assembly and to overbalance another collapsible column and the arm assembly together with the head assembly in order to implement a desired sequence of motion when the positioning system is reconfigured by a user so as to reposition the head assembly.

2. The positioning system of claim 1, wherein the counterbalancing mechanism comprises a column balancer assembly configured to counterbalance the collapsible column, wherein the column balancer assembly comprises a first tensioning element attached to a first cable, wherein the counterbalancing mechanism comprises a separate arm balancer assembly configured to counterbalance the arm assembly together with the head assembly, wherein the arm balancer assembly comprises a second tensioning element attached to a second cable, and wherein the first cable is able to move independently of the second cable, such that the column balancer assembly and the arm balancer assembly are independently operable.

3. The positioning system of claim 2, wherein the first tensioning element comprises a first spring balancer configured to counter the weight of the collapsible column, wherein the first spring balancer comprises a first spiral spring and a first variable radius pulley configured to convert the force exerted by the first spiral spring into a constant force, wherein the second tensioning element comprises a second spring balancer configured to counter the weight of the arm assembly together with the head assembly, wherein the second spring balancer comprises a second spiral spring and a second variable radius pulley configured to convert the force exerted by the second spiral spring into a constant force.

4. The positioning system of claim 3, wherein a first end of the first spiral spring is affixed to an interior surface of the fixed column, wherein a second end of the first spiral spring is attached to the first cable, and wherein the first cable extends from the first spiral spring upwardly through the interior of the fixed column and loops over the first variable radius pulley before extending downwardly through the interior of the collapsible column and attaching to a first anchor point on an interior surface of the collapsible column via a first safety latch.

5. The positioning system of claim 3, wherein a first end of the second spiral spring is affixed to an interior surface of the fixed column, wherein a second end of the second spiral spring is attached to the second cable, wherein the second cable extends upwardly from the second spiral spring through the interior of the fixed column and loops over the second variable radius pulley, before extending downwardly through the interior of the collapsible column and looping under a first fixed radius pulley, wherein the second cable extends from the first fixed radius pulley upwardly and loops over a second fixed radius pulley, before extending downwardly through the interior of a carriage of the arm assembly, and attaching to a second anchor point on an interior surface of the carriage via a second safety latch, and wherein the first and second fixed radius pulleys are mounted to the collapsible column.

6. The positioning system of claim 2, comprising an absence of tensioning elements in the collapsible column and in the arm assembly, wherein the first and second tensioning elements are at least partially housed within the fixed column.

7. The positioning system of claim 2, wherein one of the first and second tensioning elements is positioned substantially above the other of the first and second tensioning elements for reducing system footprint.

8. The positioning system of claim 2, wherein the column balancer assembly comprises a first variable radius pulley, wherein the arm balancer assembly comprises a second variable radius pulley, and wherein the first and second variable radius pulleys are mounted to the fixed column and only to the fixed column.

9. The positioning system of claim 8, comprising an absence of variable radius pulleys that are mounted to the collapsible column and an absence of variable radius pulleys that are mounted to the arm assembly.

10. The positioning system of claim 1, wherein the underbalancing and overbalancing is implemented in such a way that, in use, the mobile radiographic imaging apparatus remains statically balanced using the support of friction.

11. The positioning system of claim 1, wherein the magnitude of the underbalancing and overbalancing is less than or equal to 3N.

12. The positioning system of claim 1, further comprising an assistive motor configured to assist a user in repositioning the head assembly, wherein the motor is configured to receive feedback from a force sensor positioned to sense a force imparted by a user for repositioning the radiographic head assembly using the positioning system.

13. The positioning system of claim 1, configured to provide static balancing of the mobile radiographic imaging apparatus in all configurations of the positioning system.

14. A mobile radiography system, comprising:
   a positioning system comprising:
      a fixed column mountable to a chassis of a transport cart, the fixed column supporting a collapsible column that can be extended and retracted relative to the fixed column, the collapsible column supporting an arm assembly that can be translated relative to the collapsible column, the arm assembly being configured to support a radiographic head assembly; and
      a counterbalancing mechanism which is configured to counterbalance the collapsible column independently of the arm assembly together with the head assembly, wherein the counterbalancing mechanism is configured to underbalance the collapsible column and the arm assembly together with the radiographic head assembly and to overbalance another collapsible column and the arm assembly together with the head assembly in order to implement a desired sequence of motion when the positioning system is reconfigured by a user so as to reposition the head assembly;
   a transport cart having a chassis to which the fixed column of the positioning system is mounted; and
   a radiographic head assembly supported by the arm assembly of the positioning system.

* * * * *